US012588949B2

(12) United States Patent
Xuan et al.

(10) Patent No.: US 12,588,949 B2
(45) Date of Patent: Mar. 31, 2026

(54) LASER ABLATION WITH ELECTROMAGNETIC ENERGY FEEDBACK

(71) Applicant: Boston Scientific Scimed, Inc., Maple Grove, MN (US)

(72) Inventors: Rongwei Jason Xuan, Fremont, CA (US); Brian P. Watschke, Minneapolis, MN (US); Douglas L. Evans, Andover, MN (US); Guangjian Wang, Falcon Heights, MN (US); Wen-Jui Ray Chia, Sunnyvale, CA (US); Nathan Brown, Bloomington, MN (US); Thomas C. Hasenberg, Campbell, CA (US); Jian James Zhang, Santa Clara, CA (US); Hyun Wook Kang, Nam-gu (KR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 606 days.

(21) Appl. No.: 16/809,007

(22) Filed: Mar. 4, 2020

(65) Prior Publication Data

US 2020/0197092 A1 Jun. 25, 2020

Related U.S. Application Data

(63) Continuation of application No. 14/435,028, filed as application No. PCT/US2013/030138 on Mar. 11, 2013, now Pat. No. 10,617,470.
(Continued)

(51) Int. Cl.
| | |
|---|---|
| *A61B 18/22* | (2006.01) |
| *A61B 18/00* | (2006.01) |
| *A61B 18/20* | (2006.01) |

(52) U.S. Cl.
CPC ..... *A61B 18/22* (2013.01); *A61B 2018/00511* (2013.01); *A61B 2018/00517* (2013.01);
(Continued)

(58) Field of Classification Search
CPC ..................... A61B 18/22; A61B 2018/00988
See application file for complete search history.

(56) References Cited

U.S. PATENT DOCUMENTS

| | | | |
|---|---|---|---|
| 4,316,467 A | 2/1982 | Muckerheide |
| 4,641,650 A | 2/1987 | Mok |
(Continued)

FOREIGN PATENT DOCUMENTS

WO WO 2014/062219 A1 4/2014

OTHER PUBLICATIONS

International search report and Written Opinion of PCT/US2013/030138, mailed May 9, 2013.
(Continued)

*Primary Examiner* — Daniel L Cerioni
(74) *Attorney, Agent, or Firm* — Seager, Tufte & Wickhem, LLP

(57) ABSTRACT

Embodiments of a surgical laser system comprise a laser source (102), a laser fiber (104), a photodetector (106) and a controller (108). The laser source is configured to generate laser energy (1 10). The laser fiber is optically coupled to the laser source and is configured to discharge the laser energy generated by the laser source. The photodetector is configured to generate an output signal (1 12) that is indicative of an intensity level of electromagnetic energy feedback (114) that is produced in response to the discharge of the laser energy. The controller is configured to control the laser source based on the output signal.

20 Claims, 5 Drawing Sheets

Related U.S. Application Data

(60) Provisional application No. 61/758,839, filed on Jan. 31, 2013, provisional application No. 61/714,446, filed on Oct. 16, 2012.

(52) U.S. Cl.
CPC ............... *A61B 2018/00547* (2013.01); *A61B 2018/00577* (2013.01); *A61B 2018/00589* (2013.01); *A61B 2018/00601* (2013.01); *A61B 2018/00625* (2013.01); *A61B 2018/00642* (2013.01); *A61B 2018/00666* (2013.01); *A61B 2018/00678* (2013.01); *A61B 2018/00702* (2013.01); *A61B 2018/00708* (2013.01); *A61B 2018/00732* (2013.01); *A61B 2018/00785* (2013.01); *A61B 2018/00898* (2013.01); *A61B 2018/00904* (2013.01); *A61B 2018/00988* (2013.01); *A61B 2018/20361* (2017.05); *A61B 2018/2272* (2013.01)

(56) References Cited

U.S. PATENT DOCUMENTS

| | | | |
|---|---|---|---|
| 4,939,336 | A | 7/1990 | Meyer et al. |
| 5,009,658 | A | 4/1991 | Damgaard-Iversen et al. |
| 5,795,295 | A | 8/1998 | Hellmuth et al. |
| 5,820,627 | A | 10/1998 | Rosen et al. |
| 5,847,400 | A | 12/1998 | Kain et al. |
| 6,575,912 | B1 | 6/2003 | Turcott |
| 7,104,983 | B2 | 9/2006 | Grasso, III et al. |
| 7,869,016 | B2 | 1/2011 | Mitchell et al. |
| 2005/0189503 | A1* | 9/2005 | Jamieson ............... G06V 10/56 250/559.4 |
| 2006/0106317 | A1 | 5/2006 | McConnell et al. |
| 2006/0291510 | A1* | 12/2006 | Juluri .................... H01S 5/0683 372/29.011 |
| 2007/0229080 | A1 | 10/2007 | Weiss et al. |
| 2008/0243076 | A1 | 10/2008 | Goldan et al. |
| 2009/0076488 | A1* | 3/2009 | Welches ................. A61B 18/22 606/14 |
| 2009/0175302 | A1 | 7/2009 | Bazzani et al. |
| 2010/0053631 | A1* | 3/2010 | Kitamura ............... G01C 19/72 356/461 |
| 2010/0286674 | A1 | 11/2010 | Ben-Yaker |
| 2011/0208273 | A1 | 8/2011 | Fortuna et al. |
| 2014/0188096 | A1* | 7/2014 | Chia .................... G02B 6/3812 606/16 |
| 2015/0289937 | A1 | 10/2015 | Chia et al. |

OTHER PUBLICATIONS

U.S. Appl. No. 61/615,958, filed Mar. 27, 2012.
U.S. Appl. No. 61/648,327, filed May 17, 2012.
U.S. Appl. No. 61/614,143, filed Mar. 22, 2012.
U.S. Appl. No. 61/758,839, filed Jan. 31, 2013.

* cited by examiner

LASER ABLATION WITH ELECTROMAGNETIC ENERGY FEEDBACK

CROSS-REFERENCE TO RELATED APPLICATIONS

This patent application is a continuation of and claims the benefit of priority to U.S. application Ser. No. 14/435,028, filed Apr. 10, 2015, which is a 371 National Stage Entry of International Application No. PCT/US2013/030138, filed Mar. 11, 2013, which claims the benefit of U.S. Provisional Application No. 61/758,839, filed Jan. 31, 2013, and U.S. Provisional Application No. 61/714,446, filed Oct. 16, 2012, the contents of each of which is incorporated herein by reference in its entirety.

BACKGROUND

Embodiments of the present invention generally relate to surgical laser systems and methods of controlling such systems.

Surgical laser systems have been used in various practice areas, such as, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of laser energy as part of the treatment protocol to cut, vaporize or ablating targeted tissue, such as cancerous cells and prostate tissue, for example. Healthy tissue may be inadvertently exposed to the laser energy if the laser energy is directed to the wrong location, or if the laser energy passes through the tissue or object targeted for treatment, for example. This may damage the healthy tissue.

Improvements to such surgical laser treatments are desired, such as safety improvements that assist in reducing the exposure of healthy or non-targeted tissue to laser energy during a laser treatment.

SUMMARY

Figure 1:
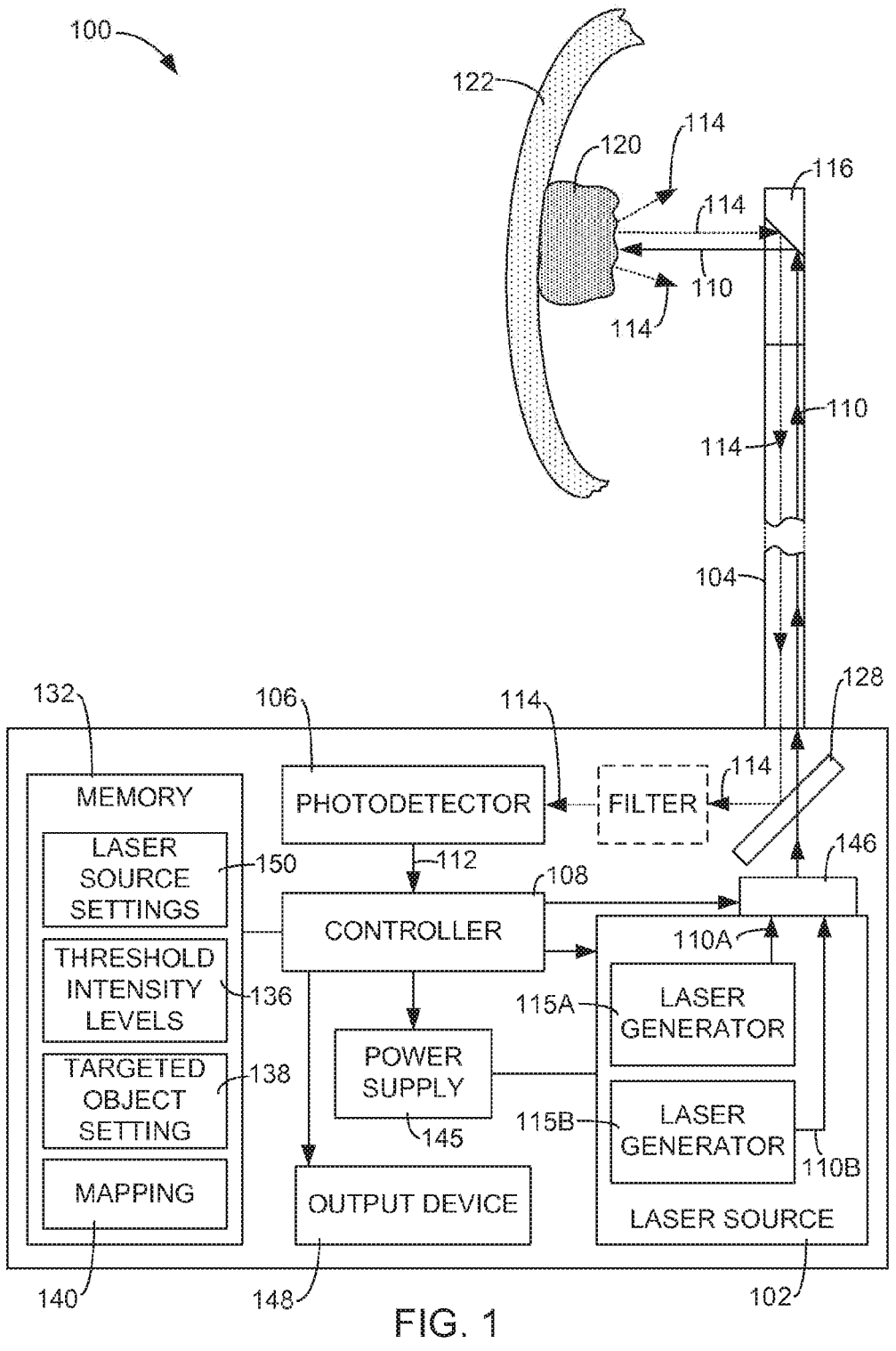
FIG. 1 is a simplified diagram of a surgical laser system in accordance with embodiments of the invention performing a surgical laser treatment.

Embodiments of the invention are directed to a surgical laser system and methods of controlling the laser system to perform a laser treatment on a patient. In some embodiments, the surgical laser system includes a laser source, a laser fiber, a photodetector and a controller. The laser source is configured to generate laser energy based on laser source settings. The laser fiber is optically coupled to the laser source and is configured to discharge the laser energy generated by the laser source. The photodetector is configured to generate an output signal indicative of an intensity level of electromagnetic energy feedback produced in response to the discharge of the laser energy. The controller is configured to control the laser source based on the output signal.

In some embodiments, the controller is configured to enable or disable the laser source based on the output signal. In some embodiments, the laser source is configured to generate the laser energy based on laser source settings, and the controller is configured to adjust at least one of the laser source settings based on the output. In some embodiments, the laser source settings include a wavelength of the laser energy, a power level of the laser energy, a pulse width of the laser energy, and/or a pulse repetition rate of the laser energy.

In some embodiments, the electromagnetic energy feedback is delivered to the photodetector through the laser fiber. In some embodiments, the electromagnetic energy feedback comprises auto-fluorescence generated by an object in response to exposure to the laser energy. In some embodiments, the electromagnetic energy feedback comprises a reflection of the laser energy.

In some embodiments, the system comprises a filter configured to filter the electromagnetic energy feedback and output filtered electromagnetic energy feedback to the photodetector.

In some embodiments, the surgical laser system comprises memory containing one or more threshold intensity levels. In some embodiments, the controller is configured to compare the intensity level indicated by the output signal to the one or more threshold intensity levels stored in the memory. In some embodiments, the controller is configured to compare the intensity level indicated by the output signal to one of the threshold intensity levels stored in the memory that corresponds to a targeted object setting. In some embodiments, the memory contains a mapping of targeted object settings to corresponding threshold intensity levels.

In some embodiments of the method, laser energy is generated using a laser source. The laser energy is discharged through a laser fiber. Electromagnetic energy feedback produced in response to discharging the laser energy is delivered to a photodetector. An output signal from the photodetector is analyzed using a controller. The controller controls the laser source responsive to analyzing the output signal.

In some embodiments, the analysis of the output signal from the photodetector comprises determining whether one of a targeted object and a non-targeted object is being exposed to the laser energy based on the output signal using the controller.

In some embodiments, the control of the laser source comprises terminating the generation of laser energy or the discharge of the laser energy using the controller.

In some embodiments of the method, an audible and/or visible signal is generated using the controller.

In some embodiments, the laser energy is generated based on laser source settings. In some embodiments, the controller controls the laser source by adjusting at least one of the laser source settings. In some embodiments, the adjustment of one of the laser source settings comprises adjusting a wavelength setting, adjusting a power level setting, adjusting a pulse width setting, and/or adjusting a pulse repetition rate setting.

In some embodiments, the laser source comprises two or more laser generators each configured to generate different laser energy. The laser source settings include a laser generator setting that determines which of the laser generators is activated to generate the laser energy. The generation of the laser energy comprises generating laser energy using a first laser generator. In some embodiments, the adjustment of at least one of the laser source settings comprises adjusting the laser generator setting. In some embodiments, laser energy is generated using a second laser generator and the laser energy is discharged through the laser fiber, in response to the adjustment of the laser generator setting.

In some embodiments of the method, the generation of the laser energy comprises generating diagnostic laser energy based on the laser source settings. In some embodiments, the control of the laser source comprises adjusting at least one of the laser source settings. In some embodiments, treatment laser energy is generated using the laser source based on the adjusted laser source settings. The treatment laser energy has a higher power level than the diagnostic laser energy. The laser treatment energy is then discharged through the laser fiber and a laser treatment is performed using the treatment laser energy. In some embodiments, the laser treatment comprises tissue ablation, tissue cutting, tissue coagulation, tissue vaporization, and/or stone fragmentation. In some embodiments, the generation of the diagnostic laser energy comprises generating diagnostic laser energy using a first laser generator of the laser source. In some embodiments, the generation of the treatment laser energy comprises generating treatment laser energy using a second laser generator of the laser source.

DETAILED DESCRIPTION OF ILLUSTRATIVE EMBODIMENTS

Embodiments of the present invention generally relate to surgical laser systems and methods of controlling surgical laser systems, such as during performance of a laser treatment on a patient. Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a". "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

The computer-usable or computer-readable medium referred to herein as "memory" may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The invention is also described using flowchart illustrations and block diagrams. It will be understood that each block (of the flowcharts and block diagrams), and combinations of blocks, can be implemented by computer program instructions. These program instructions may be provided to one or more controllers each comprising one or more processor circuits, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Embodiments in the invention are directed to a surgical laser system and methods of controlling the system to perform a surgical laser treatment on a patient, such as tissue ablation, tissue cutting, kidney or bladder stone fragmentation (i.e., laser lithotripsy) or other surgical laser treatment. FIG. 1 is a simplified diagram of a surgical laser system 100 formed in accordance with embodiments of the invention.

In some embodiments, the system 100 includes a laser source 102, a laser fiber 104, a photodetector 106 and a controller 108. The laser source 102 is configured to generate laser energy, generally referred to as 110. The laser fiber 104 is optically coupled to the laser source 102, and is configured to discharge the laser energy 110 generated by the laser source 102 to a targeted treatment site. The photodetector is configured to generate an output signal 112 that is indicative of an intensity level of electromagnetic energy feedback 114 produced in response to the discharge of the laser energy 110 from the laser fiber 104. The controller 108 is configured to control the laser source 102 based on the output signal 112 from the photodetector 106. As discussed in greater detail below, the controller 108 may interrupt the generation or discharge of the laser energy 110, or adjust the laser energy 110, based on the output signal 112.

The laser source 102 may comprise one or more laser generators, generally referred to as 115, which are used to produce the laser energy 110. Each laser generator 115 may comprise conventional components, such as a laser resonator, to produce the laser energy 110 having the desired power and wavelength. In some embodiments, the laser energy 110 has a wavelength of approximately 532 nm (green). Other wavelengths of the laser energy 110 may also be used, such as laser energy having a wavelength of approximately 400-475 nm (blue laser energy), or laser energy having a wavelength of approximately 2000-2200 nm, which is suitable for performing laser lithotripsy procedures, for example. These and other wavelengths may be used for the laser energy 110 depending on the laser treatment to be performed.

In some embodiments, the laser energy 110 generated by the laser source 102 is optically coupled to the laser fiber 104 through a conventional optical coupler (not shown). The laser fiber 104 may include any conventional surgical laser waveguide, such as an optical fiber. In some embodiments, the laser fiber 104 is configured to discharge the laser energy 110 at a distal end 116. The distal end 116 of the laser fiber 104 may be configured to discharge the laser energy 110 laterally (i.e., side-fire laser fiber), as shown in FIG. 1, along the axis of the laser fiber 104 (i.e., end-fire laser fiber), or in another conventional manner.

During a surgical laser treatment, the laser energy 110 is discharged from the distal end 116 of the laser fiber 104 toward a targeted object 120 to perform the desired laser treatment on the targeted object 120. As used herein, the term "targeted object" means an object of a patient on which a laser treatment is intended to be performed, such as a tumor, prostate tissue, a kidney or bladder stone, for example.

In some embodiments, the system 100 is configured to detect exposure of non-targeted objects 122 to the laser energy 110 to reduce or prevent damaging the non-targeted objects 122. As used herein, the term "non-targeted object" means an object of a patient on which a laser treatment is not desired to be performed. For instance, during a laser treatment (i.e., cutting, vaporizing, etc.) on a targeted object 120 in the form of a tumor, the laser energy 110 may penetrate the tumor 120 to an extent where the non-targeted healthy tissue 122 becomes damaged due to exposure to the laser energy 110. Conventional surgical laser systems rely upon the surgeon to avoid damaging the healthy non-targeted tissue of the patient while fully removing or vaporizing the targeted tumor. Embodiments of the system 100 operate to maximize the effectiveness of the laser treatment on the targeted objects 120 while minimizing exposure of non-targeted objects 122 to the laser energy 110.

Figure 2:
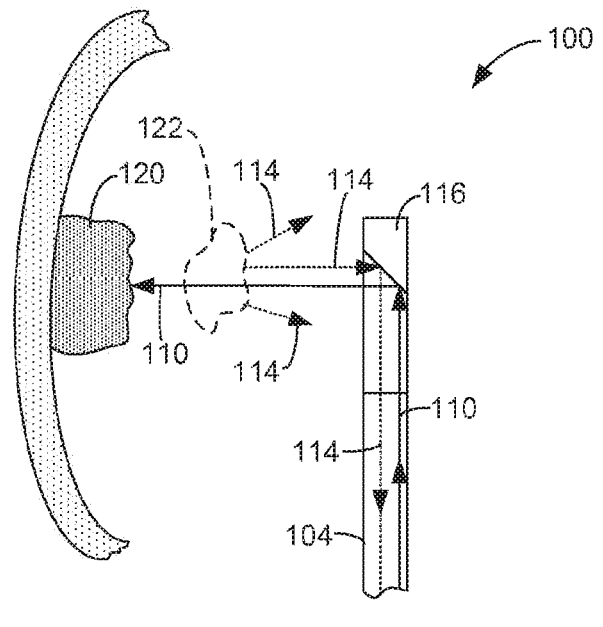
FIG. 2 is a simplified diagram of a portion of the surgical laser system of FIG. 1 performing a laser treatment.

Embodiments of the system 100 also operate to detect the exposure of non-targeted objects 122 that may disrupt a laser treatment by passing between the targeted object 120 and the distal end 116 of the laser fiber 104 thereby reducing the exposure of the targeted object 120 to the laser energy 110, as shown in the simplified illustration of a laser treatment provided in FIG. 2. For instance, a controlled cutting, vaporization or ablation treatment of a targeted object 120 may require continuous exposure of the targeted object 120 for a predetermined period of time. Interruption of the exposure by a kidney or bladder stone, or other non-targeted object 122 (illustrated in phantom), may disrupt the laser treatment. Such a disruption to the laser treatment can prevent the treatment from being performed properly.

In some embodiments, the system 100 detects the exposure of non-targeted objects 122 to the laser energy 110 based on the electromagnetic energy feedback 114 that is produced in response to the discharge of the laser energy 110 from the laser fiber 104, as illustrated in FIGS. 1 and 2. In some embodiments, the electromagnetic energy feedback 114 comprises a reflection of the laser energy 110 off a targeted object 122 (FIG. 1) or a non-targeted object 122 (FIG. 2). In some embodiments, the electromagnetic energy feedback 114 comprises auto-fluorescence generated by a targeted object 120 (FIG. 1) or a non-targeted object 122 (FIG. 2), in response to exposure of the object to the laser energy 110.

In some embodiments, the electromagnetic energy feedback 114 is fed back to the photodetector 106 through the laser fiber 104. In some embodiments, a separate optical fiber or waveguide configured to capture the electromagnetic energy feedback 114 from the treatment site is used to deliver the electromagnetic energy feedback 114 to the photodetector 106.

In some embodiments, the system 100 includes a mirror 128 that reflects the electromagnetic energy feedback 114 while allowing the laser energy 110 to pass through, as shown in FIG. 1. The electromagnetic energy feedback 114 reflected by the mirror 128 is delivered to the photodetector 106.

In some embodiments, the mirror 128 is highly transmissive over the wavelengths of the laser energy 110 and highly reflective over the wavelengths of the electromagnetic energy feedback 114. Thus, electromagnetic energy feedback 114, which comprises auto-fluorescence of targeted objects 120 or non-targeted objects 122 having a wavelength that is different from the wavelength of the laser energy 110, may be reflected by the mirror 128 to the photodetector 106 while the laser energy 110 discharged from the laser source 102 passes through the mirror to the laser fiber 104.

In some embodiments, the mirror 128 includes a central hole (not shown), through which the laser energy 110 generated by the laser source 102 is discharged. Portions of the electromagnetic energy feedback 114 impact the mirror 128 outside the edges of the hole, and are reflected by the mirror 128 to the photodetector 106. This embodiment of the mirror is particularly necessary when the electromagnetic energy feedback 114 comprises the reflected laser energy 110.

The photodetector 106 produces the output signal 112 that is indicative of an intensity of the electromagnetic energy feedback 114. In some embodiments, the system 100 includes one or more filters 130 that are configured to filter frequencies of the electromagnetic energy feedback 114, and deliver filtered electromagnetic energy feedback 114 to the photodetector 106. Exemplary embodiments of the one or more filters 130 include a low-pass filter, a high-pass filter, and/or a band-pass filter. Thus, embodiments of the output signal 112 include an output signal 112 generated by the photodetector 106 in response to the electromagnetic energy feedback 114 or the filtered electromagnetic energy feedback 114. In order to simplify the discussion, references to the output signal 112 include the output signal 112 generated in response to the filtered or unfiltered electromagnetic energy 114, unless described otherwise or inapplicable.

In some embodiments, the one or more filters 130 and photodetector 106 may be replaced with a spectrometer that analyzes the electromagnetic energy feedback 114 and outputs information, such as intensity levels of the electromagnetic energy feedback 114 over a range of wavelengths or frequencies, and/or other information. In some embodiments, the spectrometer outputs only intensity levels of the electromagnetic energy feedback 114 at certain frequencies of interest. In order to simplify the discussion, references to the output signal 112 should also be interpreted as describing embodiments in which the output signal 112 is replaced with spectrometer information generated by a spectrometer in response to an analysis of electromagnetic energy feedback 114.

The controller 108 represents conventional electronics and processors that may execute program instructions stored in memory 132 of the system 100, or other location, to perform various functions described herein. In some embodiments, the controller 108 processes (e.g., amplifies) and/or analyzes the output signal 112 to determine whether the filtered or unfiltered electromagnetic energy feedback 114 indicates that the laser energy 110 is impacting the targeted object 120 and/or whether the laser energy 110 is impacting a non-targeted object 122.

In some embodiments, a photosensitizer is introduced to the laser treatment site where the laser treatment is to occur. In some embodiments, the photosensitizer is configured to coat or be absorbed by the targeted object 120 and to enhance the absorption of the laser energy 110 by the targeted object 120. In some embodiments, the photosensitizer is selected to enhance the production of auto-fluorescence by the targeted object 120 or the non-targeted object 122 in response to exposure to the laser energy 110. Exemplary photosensitizers that may be applied to the tissue 110 include, for example, various porphyrins, chlorines/chlorophylls (including bacteriochlorins and isobacteriochlorins), and dyes (such as phthalocyanimes and naphthalocyanies) that absorb the wavelength of the selected laser energy 110. Exemplary commercially available photosensitizers that may be suitable embodiments of the invention are provided in Table 1 below.

TABLE 1

| Platform | Drug | Substance | Manufacturer |
|---|---|---|---|
| Porphyrin | Photofrin ® | HpD | Axcan Pharma, Inc. |
| Porphyrin | Levulan ® | ALA | DUSA Pharmaceuticals, Inc. |

TABLE 1-continued

| Platform | Drug | Substance | Manufacturer |
|---|---|---|---|
| Porphyrin | Metvix ® | M-ALA | PhotoCure ASA |
| Porphyrin | Visudyne ® | Vertiporfin | Novartis Pharmaceuticals |
| Texaphyrin | Antrin ® | Lutexaphyrin | Pharmacylics |
| Chlorin | Foscan ® | Temoporfin | Biolitec Pharma Ltd. |
| Chlorin | LS11 ® | Talaporfin | Light Science |
| Chlorin | Photochlor | HPPH | RPCI |
| Dye | Photosens ® | Phthalocyanine | General Physics Institute |

In some embodiments, the controller 108 compares the detected intensity level of the electromagnetic energy feedback 114 indicated by the output signal 112 to one or more threshold intensity levels 136 stored in the memory 132 or other location. The threshold intensity levels 136 may each comprise single value intensity levels, or a range of intensity levels. In some embodiments, the controller 108 determines whether a targeted object 120, or a non-targeted object 122 is being exposed to the discharged laser energy 110 based on a relationship (i.e., greater than, less than, within a range, etc.) between the detected intensity level of the electromagnetic energy feedback 114 to one or more of the threshold intensity levels 136.

In some embodiments, the system 100 includes a targeted object setting 138 stored in the memory 132 or other location. The targeted object setting 138 indicates the type of targeted object 120 intended to be exposed to the discharged laser energy 110 during a laser treatment. In some embodiments, the threshold intensity level 136 is set responsive to the targeted object setting 138. In some embodiments, this relationship between the targeted object setting 138 and the threshold intensity levels 136 is contained in a mapping 140, which identifies the threshold intensity level 136 for a given targeted object setting 138.

In some embodiments, the operator of the system 100 selects a desired target object setting 138 corresponding to the targeted object 120 and the laser procedure to be performed through a suitable input using the controller 108. For example, the targeted object setting 138 may be set to vaporize a bladder tumor of the patient. A corresponding threshold intensity level 136 is then set based on the targeted object setting using, for example, the mapping 140. During the performance of the laser treatment, the photodetector 106 produces the output signal 112 in response to the electromagnetic energy feedback 114. The controller 108 compares the detected intensity level of the electromagnetic energy feedback 114 indicated by the output signal 112 to the threshold intensity level 136 set in response to the targeted object setting 138, to determine whether the targeted tumor 120, or a non-targeted object is being exposed to the laser energy 110.

Figure 3:
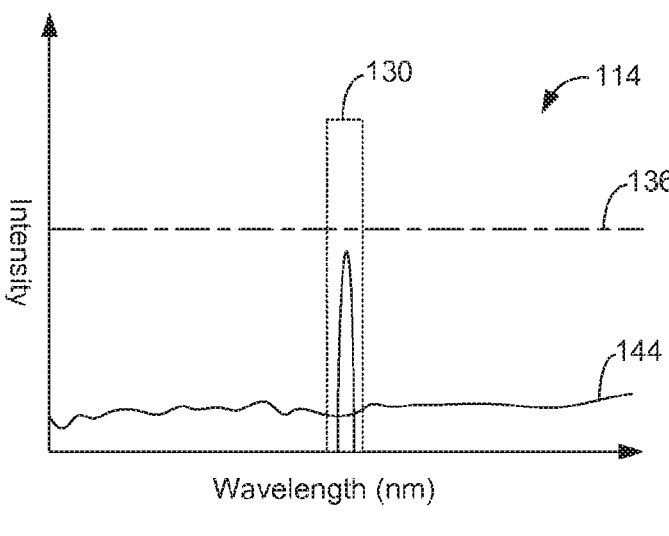
FIGS. 3-7 are charts illustrating exemplary electromagnetic energy feedback generated in response to the discharge of laser energy during a laser treatment, in accordance with embodiments of the invention.
Figure 4:
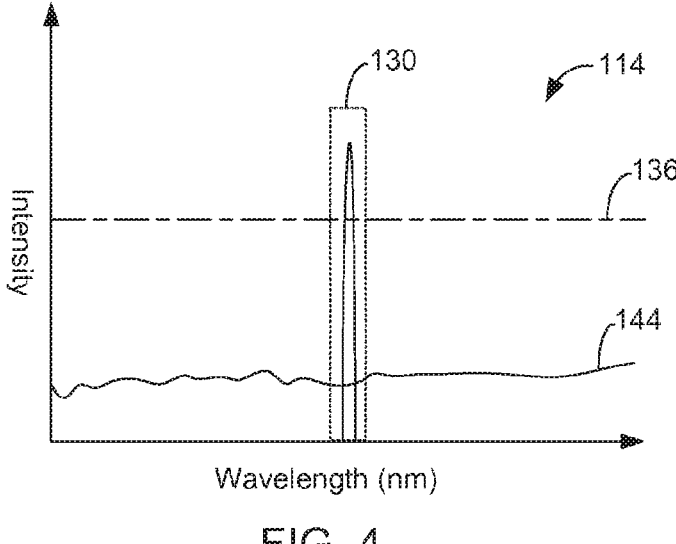

FIGS. 3 and 4 are charts illustrating intensity vs. wavelength of exemplary electromagnetic energy feedback 114 comprising the reflected laser energy 110 generated in response to the exposure of a targeted object 120, or a non-targeted object 122 during a laser treatment. In some embodiments, the output signal 112 from the photodetector 106 is indicative of the electromagnetic energy feedback 114 at a certain wavelength or frequency, or within a range of wavelengths or frequencies due to the filtering of the electromagnetic energy feedback 114 by the filter 130 (represented by box 130), or the selection of wavelengths or frequencies output from a spectrometer, as discussed above. When reflections of the laser energy 110 are used as the electromagnetic energy feedback 114, it is only necessary to focus on a very narrow wavelength band due to the laser energy 110 spanning a very narrow range of wavelengths. Accordingly, the filter 130 or spectrometer may be used to pass only the wavelengths or frequencies of the electromagnetic energy feedback 114 corresponding to the wavelength of the laser energy 110, and block frequencies associated with other sources (represented by line 144), such as auto-fluorescence of tissue exposed to the laser energy 110, illuminating light delivered to the target site, or other source.

In some embodiments, when the controller 108 determines that the intensity of the electromagnetic energy feedback 114 is below the threshold intensity level 136 (FIG. 3) based on the output signal 112, the controller 108 determines that the targeted object 120 is being exposed to the laser energy 110, and when the output signal 112 indicates that the intensity of the electromagnetic energy feedback 114 is above the threshold intensity level 136 (FIG. 4), the controller 108 determines that the non-targeted object 122 is being exposed to the laser energy. This situation may exist for a tissue cutting, ablation or vaporization treatment, such as a Benign Prostate Hyperplasia (BPH) treatment, during which there is a chance of exposing a non-targeted object 122, such as a kidney or bladder stone, to the laser energy 110, such as illustrated in FIG. 2.

Exposure of the targeted tissue 120 to the laser energy 110 produces less reflection due to the absorption of the laser energy 110 by the targeted tissue 120. As a result, the intensity of the electromagnetic energy feedback 114 is relatively low when the targeted object 120 is exposed to the laser energy 110. Thus, in some embodiments, the controller 108 determines that the targeted object 120 is being exposed to the laser energy 110 when the intensity of the electromagnetic energy feedback 114 indicated by the output signal 112 is less than the threshold intensity level 136, as shown in FIG. 3.

In some embodiments, exposure of a stone or other non-targeted object 122 results in more reflection of the laser energy 110, and higher intensity electromagnetic energy feedback 114, as compared to when the targeted object 120 is being exposed to the laser energy 110. Accordingly, in some embodiments, the controller 108 determines that the non-targeted object 122 is being exposed to the laser energy 110 when the intensity of the electromagnetic energy feedback 114 indicated by the output signal 112 is greater than the threshold intensity level 136, as shown in FIG. 4.

In some embodiments, when the controller 108 determines that the intensity of the electromagnetic energy feedback 114 is above the threshold intensity level 136 (FIG. 4) based on the output signal 112, the controller 108 determines that the targeted object 120 is being exposed to the laser energy 110, and when the output signal 112 indicates that the intensity of the electromagnetic energy feedback 114 is below the threshold intensity level 136 (FIG. 3), the controller 108 determines that the non-targeted object 122 is being exposed to the laser energy. This situation may exist for a laser lithotripsy treatment configured to fragment kidney or bladder stones (targeted object 120), during which there is a chance of exposing tissue of the patient (non-targeted object 122) to the laser energy 110. Accordingly, exposure of the targeted stone results in more reflection of the laser energy 110 and, therefore, higher intensity electromagnetic energy feedback 114, whereas exposure of non-targeted tissue results in less reflection of the laser energy 110 due to its greater absorption by the tissue, and lower intensity electromagnetic energy feedback 114.

Figure 5:
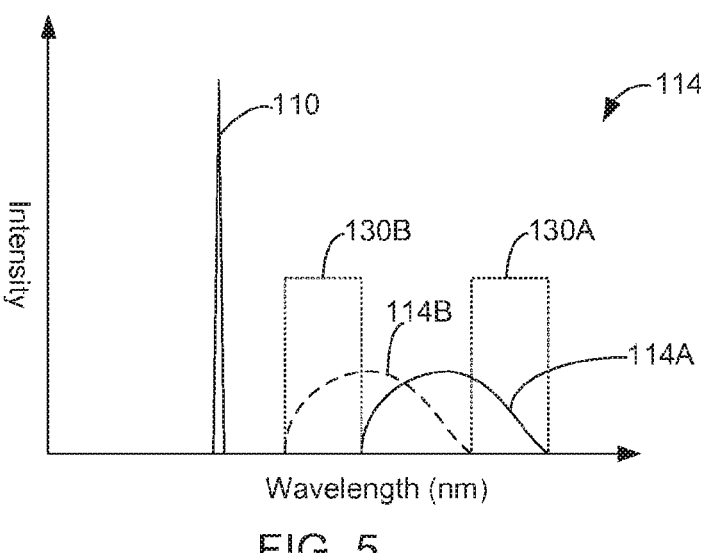
Figure 6:
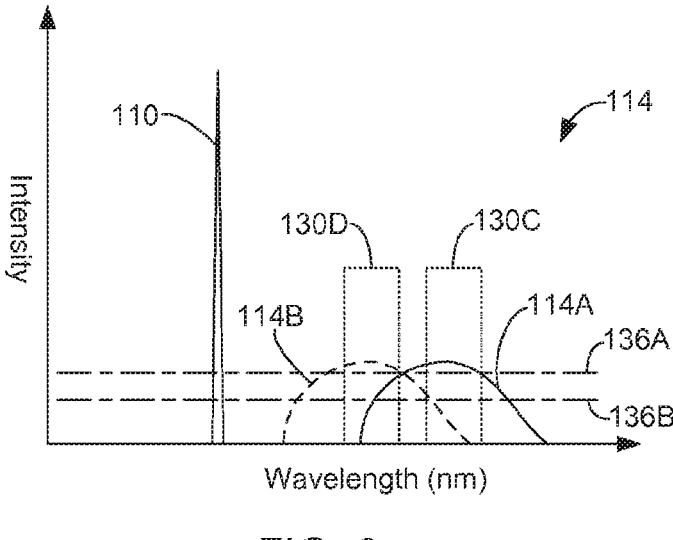
Figure 7:
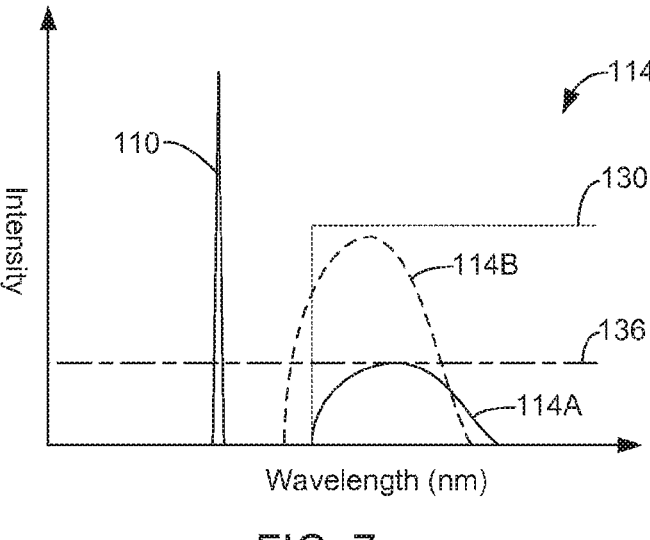

FIGS. 5-7 are charts illustrating intensity vs. wavelength of exemplary electromagnetic energy feedback 114 that comprises auto-fluorescence, such as a spectra 114A of auto-fluorescence generated by a targeted object 120 in response to exposure to the laser energy 110, and a spectra 114B of auto-fluorescence generated by non-targeted object 122 in response to exposure to the laser energy 110. Also shown in FIGS. 5-7 is the spectra of exemplary laser energy 110.

In some embodiments, the auto-florescence 114A includes a range of wavelengths that do not overlap the wavelengths of the auto-fluorescence 114B generated by the non-targeted object 122, as shown in FIG. 5. In some embodiments, the filter 130 is configured to pass a range of wavelengths corresponding to the wavelengths of the auto-fluorescence 114A that do not overlap the auto-fluorescence 114B, as indicated by box 130A. In accordance with this embodiment, when the output signal 112 produced by the photodetector 106 in response to the electromagnetic energy feedback 114 filtered by the filter 130A is greater than zero, or exceeds a threshold intensity level 136, the controller 108 determines that the targeted object 120 is being exposed to the laser energy 110.

In accordance with another embodiment, the filter 130 is configured to pass a range of wavelengths, as indicated by box 130B, spanning a portion of the auto-fluorescence spectra 114B generated by the non-targeted object 122 in response to exposure to the laser energy 110 that do not overlap the auto-fluorescence spectra 114A, as shown in FIG. 5. In accordance with this embodiment, when the output signal 112 produced by the photodetector 106 in response to the electromagnetic energy feedback 114 filtered by the filter 130B is greater than zero, or exceeds a threshold intensity level 136, the controller 108 determines that the non-targeted object 122 is being exposed to the laser energy 110.

In some embodiments, the filter 130 is configured to pass a range of wavelengths corresponding to both the auto-fluorescence spectra 114A and the auto-fluorescence spectra 114B, as shown in FIG. 6. In some embodiments, the filter 130 covers the range of wavelengths within the box 130C. In some embodiments, the controller 108 compares an intensity of the electromagnetic energy feedback 114 filtered by the filter 130C, as indicated by the output signal 112 of the photodetector 106, to a threshold intensity level 136A to determine whether the electromagnetic energy feedback 114 contains auto-fluorescence 114A generated by the targeted object 120 in response to exposure to the laser energy 110, or auto-fluorescence 114B generated by the non-targeted object 122 in response to exposure to the laser energy 110. For instance, when the intensity of the filtered electromagnetic energy feedback 114 is at or below the threshold intensity level 136A, the controller 108 can determine that the electromagnetic energy feedback 114 is being generated by a non-targeted object 122. However, when the intensity of the filtered electromagnetic energy feedback 114 is greater than the intensity level 136A, the controller 108 determines that the electromagnetic energy feedback 114 has been generated by a targeted object 120 in response to exposure to the laser energy 110.

Similarly, the filter 130 may pass a range of wavelengths within the box 130D, which covers portions of the auto-fluorescence spectra 114A and 114B respectively generated by targeted objects 120 and non-targeted objects 122 in response to exposure to the laser energy 110. In accordance with this embodiment, the controller 108 determines whether the signal 112 produced by the photodetector 106 indicates that the filtered electromagnetic energy feedback 114 filtered by the filter 130D has an intensity level that is greater or less than the threshold intensity level 136B, as shown in FIG. 6. If the filtered electromagnetic energy feedback 114 has an intensity that is less than the threshold level 136B, then the controller 108 determines that the electromagnetic energy feedback 114 has been generated by the targeted object 120 in response to exposure to the laser energy 110. If the controller 108 determines that the output signal 112 from the photodetector 106 indicates that the filtered electromagnetic energy feedback 114 has an intensity that is greater than the threshold intensity level 136B, the controller 108 determines that the electromagnetic energy feedback 114 has been generated by the non-targeted object 122 in response to exposure to the laser energy 110.

In some embodiments, the filter 130 is in the form of a high or low-pass filter that is preferably configured to remove the wavelengths corresponding to the laser energy 110. An example of this is illustrated in FIG. 7, in which the filter 130 is a high-pass filter that allows wavelengths of the electromagnetic energy feedback 114 that are greater than the wavelengths of the laser energy 110 to pass to the photodetector 106 or spectrometer. In some embodiments, the intensity of the filtered electromagnetic energy feedback 114 indicated by the output signal 112 indicates whether the targeted object 120 or the non-targeted object 122 is being exposed to the laser energy 110. For instance, when the controller 108 determines that the intensity of the filtered electromagnetic energy feedback 114 indicated by the output signal 112 is greater than a threshold intensity level 136, the controller 108 determines that the electromagnetic energy feedback 114 is produced by the non-targeted object 122 in response to exposure to the laser energy 110. When the filtered electromagnetic energy feedback 114 has an intensity level indicated by the output signal 112 that is below the threshold intensity level 136, the controller 108 determines that the electromagnetic energy feedback 114 is generated by the targeted object 120 in response to exposure to the laser energy 110.

In some embodiments, the example illustrated in FIG. 7 may be reversed such that the auto-fluorescence 114A is greater than the auto-fluorescence 114B. Here, the controller 108 determines that a targeted object 120 is being exposed to the laser energy 110 when the detected intensity of the feedback 114 is greater than the threshold 136, and the controller 108 determines that a non-targeted object 122 is being exposed to the laser energy 110 when the detected intensity of the feedback 114 is less than the threshold 136.

In some embodiments, the controller 108 is configured to control the laser source 102 based on the output signal 112 generated by the photodetector 106. In some embodiments, the controller 108 enables the discharge of the laser energy 110 through the laser fiber 104 when the controller 108 determines that the output signal 112 indicates that a targeted object 120 is being exposed to the laser energy 110, or that non-targeted objects 122 are not being exposed to the laser energy 110. When the controller 108 determines that the output signal 112 indicates that the discharged laser energy 110 is no longer impacting the targeted object 120, or is impacting the non-targeted object 122, the controller 108 prevents the laser energy 110 from being discharged by the system 100.

In some embodiments, the discharge of the laser energy 110 may be terminated or interrupted by the controller 108 by deactivating a power supply 145 that supplies power to the laser source 102. In some embodiments, the controller 108 terminates the discharge of the laser energy 110 through the laser fiber 104 by controlling a shutter mechanism 146 through which the laser energy 110 is discharged from the laser source 102 to the laser fiber 104.

In some embodiments, the controller 108 controls an output device 148 (FIG. 1) to issue a warning to the physician performing the laser treatment when the controller 108 determines that the targeted object 120 is not being exposed to the laser energy 110, and/or a non-targeted object 122 is being exposed to the laser energy 110. In some embodiments, the warning is in the form of an audible signal, such as an alarm, and/or a visible signal, such as a flashing light.

In some embodiments, the system 100 includes laser source settings 150, as shown in FIG. 1, which define the laser energy 110 to be generated by the laser source 102 and discharged through the laser fiber 104. The laser source settings 150 may be stored in the memory 132 of the system 100, memory (not shown) of the laser source 102, or other location. In some embodiments, a controller of the laser source 102, which may be represented by controller 108, configures the one or more laser generators 115 to output laser energy 110 based on the laser source settings 150. Exemplar embodiments of the laser source settings 150 include a wavelength of the laser energy, a power level of the laser energy, a pulse width of the laser energy, a pulse repetition rate of the laser energy, or other setting. In some embodiments, the laser source settings 150 include an enable or disable setting for each of the laser generators 115. Thus, embodiments of the laser source settings control which of the laser generators 115 are activated during a laser treatment, as well as the laser energy 110 generated by the activated laser generator 115.

In some embodiments, the controller 108 controls the laser source settings 150 in response to the output signal 112. In some embodiments, the controller 108 adjusts the one or more laser source settings to change the output laser 110 discharged from the laser source 102. In some embodiments, the controller 108 may adjust the laser source settings 150 to disable the active laser generator 115 of the laser source 102 to prevent the further discharge of laser energy 110 from the laser fiber 104 when the output signal 112 from the photodetector 106 indicates that targeted objects 120 are not being exposed to the laser energy 110, and/or non-targeted objects 122 are being exposed to the laser energy 110 discharged from the laser fiber 104.

In some embodiments, the system 100 is configured to determine or automatically select a laser treatment for targeted tissue or objects using the electromagnetic energy feedback 114. In some embodiments, the controller 108 controls the laser source settings 150 to cause the laser source to output laser energy 110 in the form of diagnostic laser energy that preferably has an energy level that is insufficient or unlikely to cause damage to tissue of the patient. In some embodiments, the diagnostic laser energy 110 has a power level in the range of 0.1 Mw-500 mW. In some embodiments, the diagnostic laser energy 110 may be produced by one of a plurality of laser generators 115 of the laser source 102. For instance, laser generator 115A may be configured to produce the desired diagnostic laser energy 110A that is discharged from the laser fiber 104 during a diagnostic stage of the laser treatment, as shown in FIG. 1. The laser generator 115A may be configured and/or enabled by the controller 108 using the laser source settings 150.

In some embodiments, reflections of the diagnostic laser energy 110 off a targeted object 120 or auto-fluorescence generated by the targeted object 120 in response to exposure to the diagnostic laser energy 110, is fed back to the photodetector 106 as laser energy feedback 114, as shown in FIG. 1. In some embodiments, the controller 108 uses the output signal 112 generated by the photodetector 106 (or spectrometer) in response to the laser energy feedback 114 to automatically select a laser treatment for the targeted object 120. In some embodiments, the mapping 140 may comprise an identification of a laser treatment or laser source settings 150 corresponding to the treatment, and corresponding intensity levels of the electromagnetic energy feedback 114 indicated by the output signal 112 generated responsive to exposure of targeted objects to the diagnostic laser energy 110. In some embodiments, the controller 108 uses the intensity level indicated by this diagnostic output signal 112 to identify the corresponding treatment or laser source settings 150. In some embodiments, the controller 108 adjusts one or more of the laser source settings 150 such that the laser source 102 discharges the laser energy 110 needed to perform the laser treatment. The laser treatment is then performed based on the adjusted laser source settings 150.

Thus, in an exemplary laser treatment performed by the system 100, the laser source settings 150 may initially be set up such that a laser generator 115A generates diagnostic laser energy 110A, which is discharged from the laser fiber 104 as laser energy 110. The electromagnetic energy feedback 114 generated in response to the exposure of a targeted object 120 to the diagnostic laser energy 110A is fed back to a photodetector 106 or spectrometer of the system 100, which outputs a signal 112 indicative of an intensity level of the electromagnetic energy feedback 114. In some embodiments, the controller 108 identifies a laser treatment or laser source settings 150 based on the output signal 112. In some embodiments, the controller 108 uses the mapping 140 to identify laser source settings corresponding to the intensity level indicated by the output signal 112. The system 100 then transitions from the diagnostic mode to a laser treatment mode, in which the controller 108 adjusts the laser source settings 150 to produce laser energy 110 configured to perform the laser treatment on the targeted object 120. In some embodiments, this involves disabling the laser generator 115A and enabling another laser generator, such as laser generator 115B, which generates laser treatment energy HOB that is used to perform the laser treatment. Alternatively, the laser source settings 150 can be used to adjust the laser energy 110A produced by the laser generator 115A, such that the laser energy 110 is capable of performing the laser treatment. As the laser treatment commences, the electromagnetic energy feedback 114 may be analyzed by the system 100 and used to control the discharge of the laser energy 110 in accordance with one or more embodiments described above.

Figure 8:
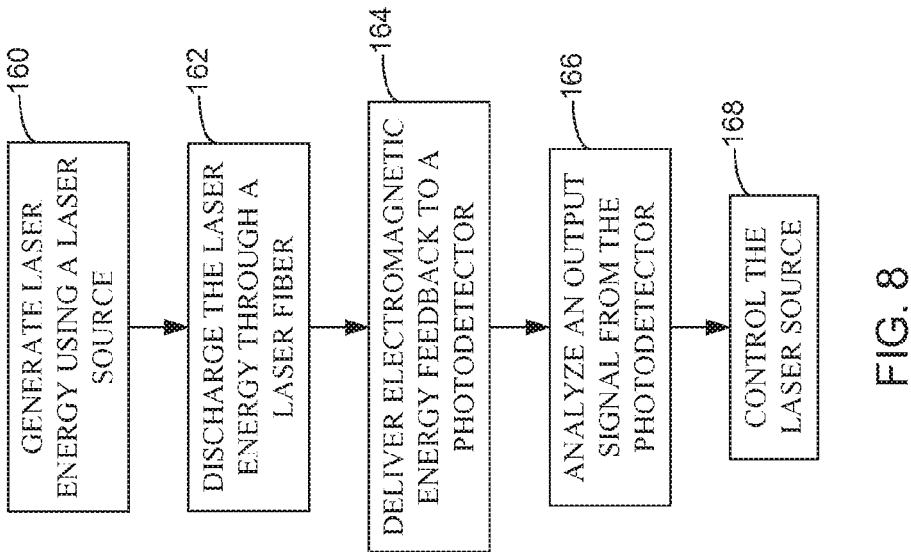
FIG. 8 is a flowchart illustrating a method of controlling a surgical laser system in accordance with embodiments of the invention.

FIG. 8 is a flowchart illustrating a method of controlling a surgical laser system, in accordance with embodiments of the invention. In some embodiments, the method involves controlling the surgical laser system 100 formed in accordance with one or more embodiments described above. At 160, laser energy 110 is generated using a laser source 102. In some embodiments of step 160, the laser energy 110 generated by the laser source 102 is in accordance with one or more laser source settings 150, as described above. At 162, the laser energy 110 is discharged through a laser fiber 104, as shown in FIG. 1. In some embodiments, the laser energy 110 is discharged from a distal end 116 of the laser fiber 104 in accordance with one or more embodiments described above.

At 164 of the method, electromagnetic energy feedback 114 is delivered to a photodetector 106 or a spectrometer. In some embodiments, the electromagnetic energy feedback 114 is delivered through the laser fiber 104 to the photodetector 106 or spectrometer. In other embodiments, the electromagnetic feedback 114 is delivered to the photodetector 106 or spectrometer through a waveguide that is separate from the optical fiber 104. In some embodiments, the electromagnetic energy feedback 114 is passed through a filter 130 before being delivered to the photodetector 106 or the spectrometer, in accordance with embodiments described above.

In some embodiments, an output signal 112 from the photodetector 106 or spectrometer, which is indicative of an intensity level of the filtered or unfiltered electromagnetic energy feedback 114, is analyzed using a controller 108, at 166 of the method. At 168, the laser source 102 is controlled responsive to step 166. In some embodiments, steps 162, 164, 166 and 168 are repeated during a laser treatment a limited number of times.

In some embodiments of step 168, the controller 108 terminates the generation of the laser energy 110 by the laser source 102, or the discharge of the laser energy 110. In some embodiments, this is accomplished by the controller 108 through the control of the power supply 145, or a shutter mechanism 146, as discussed above.

In some embodiments of step 168, the controller 108 adjusts one or more laser source settings 150 that are used to control the laser energy 110 output from the laser source 102, as described above. In some embodiments of step 168, the laser source settings 150 that are adjusted using the controller 108 include a wavelength setting, a power level setting, a pulse width setting, a pulse repetition rate setting, settings that designate which of a plurality of laser generators 115 are activated or deactivated, or other laser source setting 150.

In some embodiments, the laser source 102 comprises two or more laser generators 115, which are each configured to generate different laser energy 110. For instance, the laser source 102 may include a laser generator 115A that is configured to produce laser energy 110A, and a laser generator 115B that is configured to produce laser energy HOB, as shown in FIG. 1. In some embodiments, the laser source settings 150 include a laser generator setting that determines which of the laser generators 115 is activated to generate the laser energy 110 discharged from the laser fiber 104. In some embodiments of step 160, laser energy 110A generated by the laser generator 115A is generated and discharged through the laser fiber 104. In some embodiments, the controller 108 adjusts the laser source settings 150 following the discharge of the laser energy 110A.

In some embodiments, this adjustment of the laser source settings 150 is made responsive to steps 166 and 168, in which electromagnetic energy feedback 114 generated in response to the discharge of the laser energy 110A is analyzed using the photodetector 106 or spectrometer to produce an output signal 112 used by the controller 108 to adjust one or more of the laser source settings 150. In some embodiments, the controller 108 adjusts the laser generator setting to deactivate the laser generator 115A and activate the laser generator 115B. In some embodiments, the laser generator 115B generates laser energy HOB, which is discharged through the laser fiber 104.

In some embodiments, the laser energy 110A is diagnostic laser energy that is used to determine a laser treatment that is to be performed on targeted objects 120, as discussed above. In some embodiments, the laser energy HOB is laser treatment energy that is configured to perform a laser treatment on one or more targeted objects 120, as discussed above. In some embodiments, the treatment laser energy HOB has a higher power level than the diagnostic laser energy 110A. In some embodiments, the laser treatment performed by the treatment laser energy HOB is tissue ablation, tissue cutting, tissue coagulation, tissue vaporization, or stone fragmentation.

Figure 9:
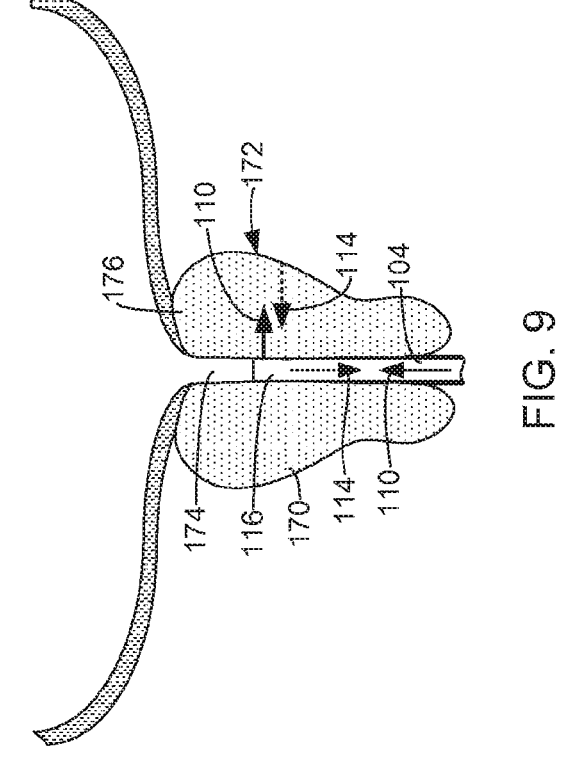
FIG. 9 is a simplified illustration of a surgical laser treatment on a prostate in accordance with embodiments of the invention.

FIG. 9 is a simplified illustration of an exemplary surgical laser treatment on a prostate 170 in accordance with embodiments of the invention. One issue with treating an enlarged prostate through laser ablation is that the laser energy 110 may perforate the prostate capsule 172. Embodiments of the system 100 are useful in preventing this perforation.

In some embodiments, the laser fiber 104 is inserted through the urethra 174 of the patient to place the distal end 116 in position to ablate the adenoma 176 of the prostate 170 (targeted object 120), as shown in FIG. 9. In one embodiment, the laser energy 110 is discharged to ablate the adenoma 176. The auto-fluorescence generated by the adenoma tissue 176 in response to the discharge of the laser energy 110, or the laser energy 110 reflected from the adenoma 176, is fed back to the photodetector 106 (or spectrometer) as electromagnetic energy feedback 114. In some embodiments, the electromagnetic energy feedback 114 is passed through a filter 130 prior to its delivery to the photodetector 106. The filter 130 is configured to pass a range of wavelengths of the electromagnetic energy feedback 114 in accordance with one or more of the embodiments described above.

The photodetector 106 generates the output signal 112, which is indicative of the intensity of the electromagnetic energy feedback 114. The controller 108 analyzes the signal 112 to determine whether the electromagnetic energy feedback 114 indicates that the laser energy 110 is impacting the adenoma tissue 176 (targeted object 120), or the prostate capsule 172 (non-targeted object 122). If it is determined that the adenoma tissue 176 is being exposed to the laser energy 110, the controller 108 allows the ablation procedure to continue by enabling the discharge of the laser energy 110 using any of the techniques described above. However, if the electromagnetic energy feedback 114 indicates that the laser energy 110 is impacting the non-targeted prostate capsule 172, or other non-targeted object, the controller 108 terminates the ablation procedure by preventing the further discharge of the laser energy 110. Accordingly, embodiments of the system 100 may be used to perform ablation treatments on the adenoma tissue 176 of the prostate while preventing perforation of the prostate capsule 172.

The above-method may also be applied to other surgical laser treatments. For instance, the method may be used in a laser treatment of bladder cancer where the tumor is targeted by the laser energy and the electromagnetic energy feedback is analyzed to prevent or reduce exposure of the non-targeted wall of the bladder to the laser energy. This allows the tumor to be treated or removed without significantly damaging or perforating the bladder wall.

Although the present invention has been described with reference to preferred embodiments, workers skilled in the art will recognize that changes may be made in form and detail without departing from the spirit and scope of the invention.

What is claimed is:

1. A controller for a surgical laser system, the controller comprising:
   a processor and a memory, the memory comprising instructions, which when executed by the processor cause the processor to:
   send a control signal to a laser source of the surgical laser system to cause the laser source to generate a laser energy at one or more first wavelengths, wherein the surgical laser system is configured to be optically coupled to a proximal end of a laser fiber such that the laser energy can be discharged from a distal end of the laser fiber toward an object as part of a lithotripsy procedure;
   receive, from a photodetector of the surgical laser system, an indication of an intensity of a feedback, wherein the photodetector is configured to be optically coupled to the proximal end of the laser fiber and wherein the feedback is at a plurality of second wavelengths different from the one or more first wavelengths;
   determine a first intensity of the feedback in a first portion of the plurality of second wavelengths;
   determine a second intensity of the feedback in a second portion of the plurality of second wavelengths different from the first portion; and
   determine whether the object is a targeted object or a non-targeted object based on the first intensity relative to a first threshold intensity and the second intensity relative to a second threshold intensity different from the first threshold intensity,
   wherein the feedback is responsive to the laser energy being incident on the object, and
   wherein the feedback is received at the distal end of the laser fiber and transmitted to the proximal end of the laser fiber.

2. The controller of claim 1, wherein the controller is further configured to enable or disable the laser source based on the determination.

3. The controller of claim 1, wherein the controller is further configured to:
   enable the laser source if the indication of the intensity is greater than or equal to the threshold intensity; and
   disable the laser source if the indication of the intensity is less than the threshold intensity.

4. The controller of claim 1, wherein the controller is further configured to adjust at least one setting of the laser source based on the determination.

5. The controller of claim 4, wherein the at least one setting includes one or more of the wavelength of the laser energy, a power level of the laser energy, a pulse width of the laser energy, or a pulse repetition rate of the laser energy.

6. The controller of claim 1, wherein the controller is further configured to control an output device to generate a warning if the object is the non-targeted object.

7. The controller of claim 1, wherein the targeted object is a kidney stone or a bladder stone.

8. At least one machine readable medium comprising a plurality of instructions that in response to being executed by circuitry of a controller for a surgical laser-system, cause the circuitry to:
   send a control signal to a laser source of the surgical laser system, the control signal to cause the laser source to generate a laser energy at one or more first wavelengths, wherein the surgical laser system is configured to be optically coupled to a proximal end of a laser fiber such that the laser energy can be discharged from a distal end of the laser fiber toward an object as part of a lithotripsy procedure;
   receive, from a photodetector of the surgical laser system, an indication of an intensity of a feedback, wherein the photodetector is configured to be optically coupled to the proximal end of the laser fiber and wherein the feedback is at a plurality of second wavelengths different from the one or more first wavelengths;
   determine a first intensity of the feedback in a first portion of the plurality of second wavelengths;

determine a second intensity of the feedback in a second portion of the plurality of second wavelengths different from the first portion; and determine whether the object is a targeted object or a non-targeted object based on the first intensity relative to a first threshold intensity and the second intensity relative to a second threshold intensity different from the first threshold intensity, wherein the feedback is responsive to the laser energy being incident on the object, wherein the feedback is received at the distal end of the laser fiber and transmitted to the proximal end of the laser fiber.

9. The at least one machine readable medium of claim 8, comprising instructions that in response to being executed by the circuitry cause the circuitry to enable or disable the laser source based on the determination.

10. The at least one machine readable medium of claim 9, comprising instructions that in response to being executed by the circuitry cause the circuitry to:

enable the laser source if the indication of the intensity is greater than or equal to the threshold intensity level; and disable the laser source if the indication of the intensity is less than the threshold intensity level.

11. The at least one machine readable medium of claim 9, comprising instructions that in response to being executed by the circuitry cause the circuitry to adjust at least one setting of the laser source based on the determination.

12. The at least one machine readable medium of claim 11, wherein the at least one setting includes one or more of the wavelength of the laser energy, a power level of the laser energy, a pulse width of the laser energy, or a pulse repetition rate of the laser energy.

13. The at least one machine readable medium of claim 9, comprising instructions that in response to being executed by the circuitry cause the circuitry to control an output device to generate a warning if the object is the non-targeted object.

14. The at least one machine readable medium of claim 9, wherein the targeted object is a kidney stone or a bladder stone.

15. The at least one machine readable medium of claim 8, wherein the feedback is autofluorescence.

16. The controller of claim 1, wherein the feedback is autofluorescence.

17. A surgical laser system, comprising:

a laser source configured to generate laser energy having one or more first wavelengths;

a laser fiber coupler to couple the laser energy to a proximal end of a laser fiber, wherein the laser energy can be discharged from a distal end of the laser fiber toward an object during a lithotripsy procedure;

a photodetector optically coupled to the proximal end of the laser fiber;

a filter disposed in an optical path between the proximal end of the laser fiber and the photodetector, wherein the filter is configured to transmit laser energy having one or more second wavelengths different from the one or more first wavelengths; and a controller comprising a processor and a memory, wherein the memory comprises instructions, which when executed by the processor cause the processor to:

send a control signal to the laser source to cause the laser source to generate the laser energy;

receive, from the photodetector, an indication of an intensity of a feedback signal, wherein the feedback is at the one or more plurality of second wavelengths different from the one or more first wavelengths;

determine a first intensity of the feedback in a first portion of the plurality of second wavelengths;

determine a second intensity of the feedback in a second portion of the plurality of second wavelengths different from the first portion; and determine whether the object is a targeted object or a non-targeted object based on the first intensity relative to a first threshold intensity and the second intensity relative to a second threshold intensity different from the first threshold intensity;

determine whether the object is a targeted object or a non-targeted object based on the indication of the intensity relative to a threshold intensity, wherein the feedback is responsive to the laser energy being incident on the object.

18. The surgical laser system of claim 17, further comprising:

a therapeutic laser source configured to generate laser energy having one or more third wavelengths, different from the one or more first wavelengths and the one or more second wavelengths, wherein the instructions, when executed by the processor cause the processor to generate a warning comprising an indication that the object is a non-targeted object, and wherein the warning is a visual warning or an audible warning.

19. The surgical laser system of claim 17, further comprising a therapeutic laser source configured to generate laser energy having one or more third wavelengths, wherein the instructions, when executed by the processor cause the processor to enable or disable the therapeutic laser source based on the determination.

20. The surgical laser system of claim 19, wherein the controller is further configured to:

enable the therapeutic laser source if the indication of the intensity is greater than or equal to the threshold intensity; and disable the therapeutic laser source if the indication of the intensity is less than the threshold intensity.

* * * * *